US010647691B2

(12) United States Patent
Erfurt et al.

(10) Patent No.: US 10,647,691 B2
(45) Date of Patent: May 12, 2020

(54) METHOD FOR PURIFYING CANNABINOID COMPOUNDS

(71) Applicant: SYMRISE AG, Holzminden (DE)

(72) Inventors: Harry Erfurt, Uslar (DE); Maria Weber, Holzminden (DE); Hans-Jürgen Niemeyer, Bevern (DE); Marcus Rudolf Götz, Oberweser (DE); Matthias Winkler, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/300,205

(22) PCT Filed: May 13, 2016

(86) PCT No.: PCT/EP2016/060905
§ 371 (c)(1),
(2) Date: Nov. 9, 2018

(87) PCT Pub. No.: WO2017/194173
PCT Pub. Date: Nov. 16, 2017

(65) Prior Publication Data
US 2019/0144414 A1    May 16, 2019

(51) Int. Cl.
*C07D 311/80*    (2006.01)
*B01D 15/18*    (2006.01)
*C07C 37/00*    (2006.01)
*C07C 67/02*    (2006.01)
*C07C 67/343*    (2006.01)

(52) U.S. Cl.
CPC .......... *C07D 311/80* (2013.01); *B01D 15/185* (2013.01); *C07C 37/002* (2013.01); *C07C 67/02* (2013.01); *C07C 67/343* (2013.01); *B01D 2215/023* (2013.01)

(58) Field of Classification Search
CPC .................................................. C07D 311/80

USPC .......................................... 549/390; 568/763
See application file for complete search history.

(56) References Cited

U.S. PATENT DOCUMENTS

| 7,449,589 | B2 * | 11/2008 | Geiser | .................. C07D 311/80 549/390 |
|---|---|---|---|---|
| 2007/0093665 | A1 | 4/2007 | Burdick et al. | |
| 2010/0298579 | A1 | 11/2010 | Steup et al. | |

FOREIGN PATENT DOCUMENTS

| WO | 2006053766 A1 | 5/2006 |
|---|---|---|
| WO | 2015032519 A1 | 3/2015 |

OTHER PUBLICATIONS

International Search Report and Written Opinion dated Sep. 13, 2016 for corresponding PCT Application No. PCT/EP2016/060905.
"What is simulated moving bed chromatography (SMB chromatography)?" Internet Citation, Amalgamated Research Inc., 2008, pp. 1-11 XP007906381.
Juza, M. et al., "Simulated moving-bed chromatography and its application to chirotechnology," Trends in Biotechnology, Elsevier Publications, Cambridge, GB, vol. 18, No. 3, 2000, pp. 108-118 XP004189111.
European Office Action dated Nov. 29, 2019 for corresponding EP Application No. 16728841.4-1110.

* cited by examiner

*Primary Examiner* — Charanjit Aulakh
(74) *Attorney, Agent, or Firm* — Polsinelli PC

(57) ABSTRACT

The present invention relates to methods for purifying one or two cannabinoid compounds using simulated moving bed chromatography, wherein the cannabinoid compound(s) is/are obtained in the extract and/or the raffinate with the total amount of isomeric impurities being below detection level. In particular, the present invention relates to methods for the purification of cannabidiol, trans-(−)-delta-9-tetrahydrocannabinol, cannabidivarin, trans-(−)-delta-9-tetrahydrocannabivarin and cannabigerol which have been obtained by enantiopure synthesis.

20 Claims, 5 Drawing Sheets

METHOD FOR PURIFYING CANNABINOID COMPOUNDS

CROSS-REFERENCE TO RELATED APPLICATIONS

This application is a national stage application (under 35 U.S.C. § 371) of PCT/EP2016/060905, filed May 13, 2016, which is incorporated herein by reference in its entirety.

The present invention relates to methods for purifying one or two cannabinoid compounds using simulated moving bed chromatography, wherein the cannabinoid compound(s) is/are obtained in the extract and/or the raffinate with the total amount of isomeric impurities being below detection level. In particular, the present invention relates to methods for the purification of cannabidiol, trans-(−)delta-9-tetrahydrocannabinol, cannabidivarin, trans-(−)-delta-9-tetrahydrocannabivarin and cannabigerol which have been obtained by enantiopure synthesis. Furthermore, the present invention also relates to an extract and/or raffinate which is/are obtained or obtainable by the method according to the invention.

Since the discovery of the endogenous cannabinoid system with its functional significance in terms of the regulation and modulation of the immune as well as the nervous system, there is an ongoing need for natural and artificial cannabinoids for their selective, pharmaceutical control. In particular, because of their different medical functions, there is a need for targeted, separate stimulation of the cannabinoid receptors CB1, which are mainly found in neurons, in highest density in basal ganglia, in the hippocampus and the cerebellum, and of the cannabinoid receptors CB2, which are mainly found on cells of the immune system and on cells that are involved in bone formation and bone loss.

The cannabinoid receptors CB1 and CB2 are presumed to be the accepted sites of action of molecules with a cannabinoid structure. Even though further receptors are discussed as potential CB3 receptors, it is assumed that the main effects are mediated via CB1 and CB2. Delta-9-tetrahydrocannabinol (delta-9-THC), endogenous cannabinoids and a multitude of synthetic cannabinoids connect to said receptors and exert through them an effect on the cells (Pertwee, R. G. et al. *Pharmacol. Rev.* 2010, 62, 588-631).

CB1 and CB2 are members of the superfamily of the G protein coupled receptors (GPCRs). More precisely, the receptors inhibit the adenylate cyclase via the heteromeric G protein and activate the mitogenically activated protein kinase (Howlett, A. C. et al. *Pharmacol. Rev.* 2002, 54, 161-202; Howlett, A. C. *Handb. Exp. Pharmacol.* 2005, 168, 53-79). In terms of the CB1 receptor it is further described that it can modulate potassium flows via ion channels of the A-type and calcium flows via N as well as P/Q-type channels. Furthermore, CB1 receptors are able to transfer signals to the expressing cells via $G_s$ proteins (Glass, M., Felder, C. C. *J. Neurosci.* 1997; 17, 5327-5333; Maneuf, Y. P., Brotchie, J. M. *J. Pharmacol.* 1997; 120, 1397-1398; Calandra, B. et al. *Eur. J. Pharmacol.* 1999; 374, 445-455; Jarrahian, A. et al. *J. Pharmacol. Exp. Ther.* 2004, 308, 880-886).

The ability of CB1 and CB2 to transfer signals via $G_{i/o}$ and further downstream via inhibition of the adenylate cyclase, is used in the so-called [$^{35}$S]GTP gammaS binding assay and the cAMP assay (Howlett, A. C. et al. *Pharmacol. Rev.* 2002, 54, 161-202; Pertwee, R. G. *Handb. Exp. Pharmacol.* 2005a, 168, 1-51) to analyze the binding and signal transduction of cannabinoids.

CB1 receptors have at their disposal an orthosteric as well as one or multiple allosteric binding site(s), which are considered as potential sites of action for ligands (Price, M. R. et al. *Mol. Pharmacol.* 2005a, 68, 1484-1495; Adam, L. et al. *17th Annual Symposium of the Cannabinoids,* 2007, S. 86; Horswill, J. G. et al. *J. Pharmacol.* 2007, 152, 805-814; Navarro, H. A. et al. *J. Pharmacol.* 2009, 156, 1178-1184). CB1 receptors are mainly found on the terminal ends of central and peripheral neurons, where they usually impart an inhibition of excitatory and inhibitory neurotransmitters (Howlett, A. C. et al. *Pharmacol. Rev.* 2002, 54, 161-202; Pertwee, R. G., Ross, R. A. *Prostaglandins Leukot Essent Fatty Acids,* 2002, 66, 101-121; Szabo, B., Schlicker, E. *Handb. Exp. Pharmacol.* 2005, 168, 327-365). The distribution of these receptors in the central nervous system is in such a way that their activation can influence different cognitive processes (e.g. alertness and memory, different motor functions and pain perception).

CB2 receptors are mainly localized, as mentioned before, in immune cells. Once they get activated, they modulate cell migration and the release of cytokines inside and outside the brain (Howlett, A. C. et al. *Pharmacol. Rev.* 2002, 54, 161-202; Cabral, G. A., Staab, A. *Handb. Exp. Pharmacol.* 2005, 168, 385-423; Pertwee, R. G. *Handb. Exp. Pharmacol.* 2005a, 168, 1-51).

There is also some evidence that firstly CB1 receptors are expressed by nonneuronal cells (including immune cells) (Howlett, A. C. et al. *Pharmacol. Rev.* 2002, 54, 161-202) and that secondly CB2 receptors are expressed by some cells inside and outside the brain (Skaper, S. D. et al. *Proc. Natl. Acad. Sci. USA* 1996, 93, 3984-3989; Ross, R. A. et al. *Neuropharmacology* 2001a, 40, 221-232; Van Sickle, M. D. et al. *Science* 2005, 310, 329-332; Wotherspoon, G. et al. *Neuroscience* 2005, 135, 235-245; Beltramo, M. et al. *Eur. J. Neurosci.* 2006, 23, 1530-1538; Gong, J. P. et al. *Brain Res.* 2006, 1071, 10-23; Baek, J. H. et al. *Acta Otolaryngol* 2008, 128, 961-967).

Known compounds, which have been proven to have an affinity for the aforementioned receptors CB1 and CB2, are amongst others cannabidiol (CBD) and certain chemical derivatives thereof.

In particular the active compound delta-9-tetrahydrocannabinol (delta-9-THC) from the *cannabis* plant has become a focus of attention in the last couple of years. Reduced to only its psycho-active effects in the past, recent studies show a more diverse range of effects. Applications in cancer and HIV therapy as well as in the treatment of multiple sclerosis are found. The (−)-enantiomer has been found to be the more active one (Jones, G. et al., *Biochem. Pharmacol.,* 1974, 23: 439; Roth, S. H., *Can. J. Physiol. Pharmacol.,* 1978, 56: 968; Martin, B. R. et al., *Life Sciences,* 1981, 29: 565; Reichman, M. et al. *Mol. Pharmacol.,* 1988, 34: 823; Reichman, M. et al., *Mol. Pharmacol.,* 1991, 40: 547). Therefore an enantiopure product is desirable. Since the isolation of pure trans-(−)-delta-9-THC from *Cannabis sativa* or indica is a very time consuming and expensive process (WO 2002/045115 A1), trans-(−)-delta-9-THC is more and more synthetically produced under the name dronabinol. This is either done in a partially synthetic way by conversion of the precursor isolated from the *cannabis* plant, trans-(−)-cannabidiol, to dronabinol (WO 2002/045115 A1) or fully synthetic as described in EP 2842933 B1.

Different cannabinoid compounds and methods for their manufacture are known from the prior art.

Korte et al. (Tetrahedron Letters, 1968, 3, 145-7) describe cannabidivarin for the first time and propose a synthesis analogous to the one by Petrzilka et al. (Helvetica Chimica Acta, 1967, 50, 719-723). However, only low yields can be achieved this way.

Also Crombie et al. (Phytochemistry 1975, 4, 11975) describe the synthesis of cannabidivarin in small scale as condensation of divarin with para-menthadienol. The synthesis in dried CH$_2$Cl$_2$, saturated with PTSA, however, is not very selective and the resulting products are obtained at uneconomical proportions. Tetrahydrocannabivarin (here denoted delta-1-tetrahydrocannabivarol) is generated the same way at higher temperatures and at an uneconomical concentration in a multiple compound mixture.

WO 2006/136273 describes a method for the manufacture of dronabinol ((denoted (6a R-trans)-6a,7,8,10a-tetrahydro-6,6,9-trimethyl-3-pentyl-6 Hdibenzo[b,d]pyran-1-ol, $\Delta^9$-tetrahydrocannabinol ($\Delta^9$-THC) in the WO document), nowadays according to IUPAC also denoted (6aR,10aR)-6,6,9-trimethyl-3-pentyl-6a,7,8,10a-tetrahydro-6H-benzo[c]chromen-1-ol or delta-9-tetrahydrocannabinol, delta-9-THC or Δ-9-THC) from cannabidiol (CBD) via cyclization of cannabidiol (CBD) (2-[1R-3-methyl-6-(1-methylethenyl)-2-cyclohexene-1-yl]-5-pentyl-1,3-benzenediol) to yield delta-9-THC. The described method is characterized in that cannabidiol (CBD) is provided in an organic solvent and is heated and cyclized to delta-9-THC in the presence of a molecular sieve. It is stated in WO 2006/136273 that the used molecular sieve exhibits, besides the drying properties that have been described so far, strong catalytic properties, which are in the focus of the described conversion. Cyclizations that can only be performed in the presence of a Lewis acid catalyst are usually significantly slower and deliver worse yields of delta-9-THC than cyclizations that are performed in the presence of a molecular sieve.

Further types of syntheses are described in the literature, e.g. by Crombie et al. *Chem. Research* 1977, 114, 1301-1345. More recent synthesis methods are disclosed inter alia in EP 2314580. The method for the manufacture of cannabinoids described therein, is supposed to be applicable to all stereoisomers and homologs of cannabinoids and consists of two and three chemical synthesis steps, respectively. In a first step, alkyl resorcylic acid esters (6-alkyl-2,4-dihydroxybenzoic acid ester) are thereby condensed with unsaturated hydrocarbons, alcohols, ketones (and their derivatives such as enol esters, enol ethers and ketals, respectively) to the corresponding 6-alkyl-2,4-dihydroxybenzoic acid esters that are substituted at the 3-position. In a second step, the ester function-containing intermediates that were produced in the first step are subjected to a decarboxylating saponification, giving rise to the corresponding ester-free cannabinoids. If necessary, an acid catalyzed rearrangement is carried out in a third step. This isomerization may be e.g. the ring closure of the pyran ring of CBD to give dronabinol, but also the rearrangement of a double bond like e.g. the reorganization of delta-9 to delta-8-THC or an acid catalyzed epimerization like the rearrangement of cis-9-keto-cannabinoids to the corresponding trans-compounds.

U.S. Pat. No. 5,342,971 describes a method for the manufacture of dronabinol and of the related dibenzo[b,d]pyrans. These are produced, according to the abstract, through heating of a dihydroxybenzoic acid derivative in the presence of a Lewis acid catalyst and an inert non-polar solvent, in which indeed the dihydroxybenzoic acid is soluble, but the Lewis acid catalyst is insoluble or only very slightly soluble.

EP 2842933 B1 discloses a method for synthesizing delta-9-THC starting from menthadienol. In a first step, menthadienol is reacted with an olivetolic acid ester to a cannabidiolic acid ester. This ester is then subjected to a transesterification and the product is saponified and decarboxylated to cannabidiol. In the last step, cannabidiol is cyclised to trans-(-)-delta-9-THC in enantiopure form.

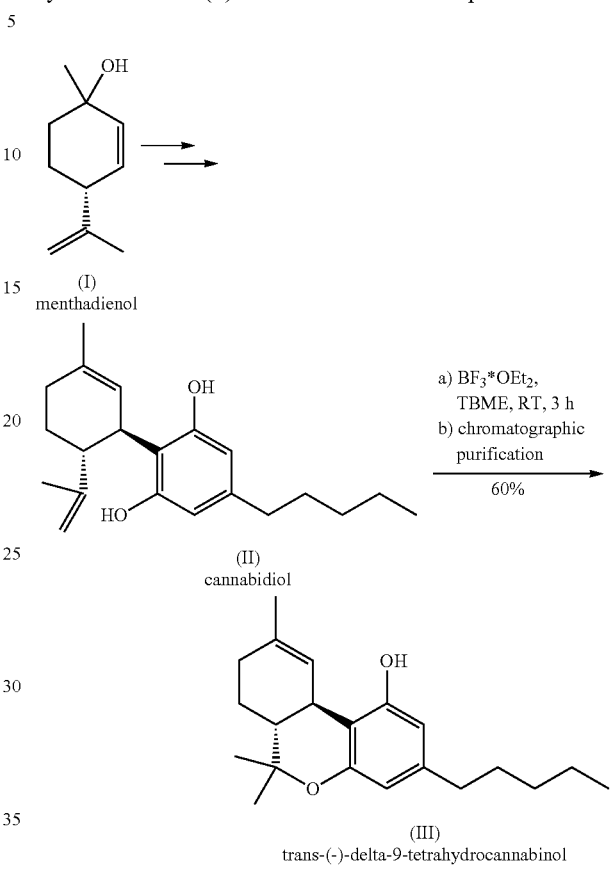

Details of the synthesis of delta-9-THC according to EP 2842933 B1 can be found in example 1.

Analogously, a synthesis of cannabidivarin (CBDV) and tetrahydrocannabivarin (THCV) starting with reacting menthadienol with a divarinic acid ester, followed by transesterification, saponification and decarboxylation to cannabidivarin and subsequent cyclisation to tetrahydrocannabivarin is described in European patent application EP 15156750.0. The product is also obtained in enantiopure form as trans-(-)-delta-9-THCV.

An example of the synthesis steps for cannabidivarin (CBDV) and tetrahydrocannabivarin (THCV) as described in European patent application EP 15156750.0 is shown schematically below. Reaction conditions can be inferred from example 2.

1. Coupling Step:

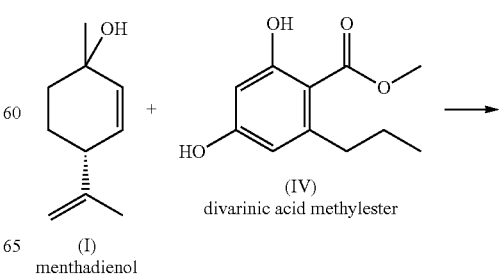

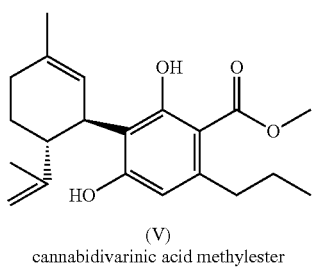

(V)
cannabidivarinic acid methylester

2. Transesterification Step:

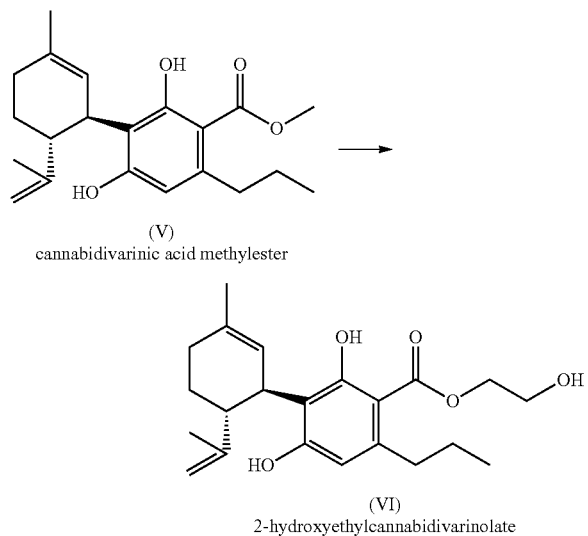

3. Saponification/Decarboxylation Step

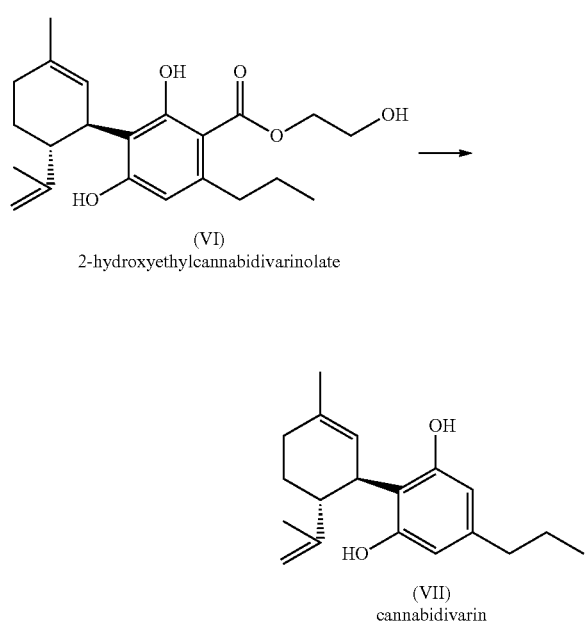

4. Cyclization Step

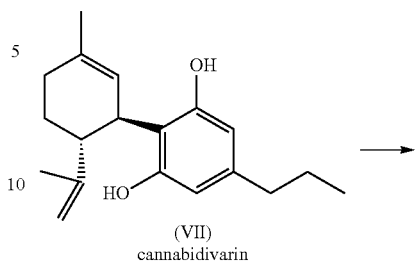

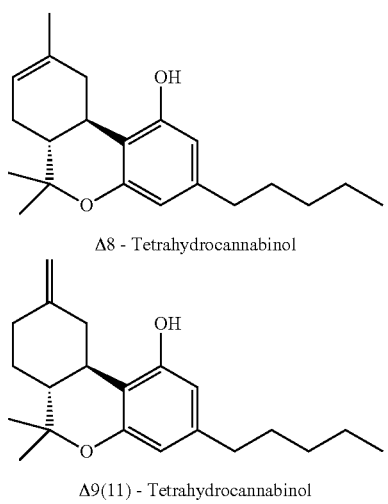

The raw product generated by the above mentioned synthesis according to EP 2842933 B1 has a delta-9-THC content of 65-75%, as well as 20-30% of the isomer delta-8-tetrahydrocannabinol as main impurity.

The purification of trans-(−)-delta-9-THC proves difficult because it can not be obtained in crystalline form. Pure delta-9-THC is a slightly yellow, air-sensitive resin. Therefore, a crystallization as with the related cannabinoids, cannabidiol or cannabidivarin is not possible when an enantiopure product is desired. Distillation is also not feasible due to the high boiling point (about 200° C. at 0.02 mbar) and its thermal instability. A particular complication is the presence of structurally very similar compounds with almost identical chemical and physical properties (polarity, boiling point etc.), which may impede purification, such as the two isomers delta-8-tetrahydrocannabinol and delta-9(11)-tetrahydrocannabinol.

The same problems arise for the raw product obtained by the synthesis of THCV as described above, where the corresponding isomers are formed.

For these reasons, expensive and time consuming chromatographic methods are employed.

WO 2002/062782 A1 discloses a method for the production of dronabinol starting with the isolation of cannabidiol from fibrous hemp, which is then chemically cyclised. According to the examples of WO 2002/062782, the resulting reaction mixture comprises up to 86% of dronabinol, which is then isolated chromatographically on a silica gel column. The solvent is removed and the product is purified by high vacuum distillation or crystallization. However, as indicated above, distillation of dronabinol is highly inefficient because of its thermal instability and crystallization is only possible with an enantiomeric mixture.

According to WO 2009/133376 A1, delta-9-THC and delta-9-THC carboxylic acid are extracted from plant material and then the delta-9-THC carboxylic acid is converted to delta-9-THC in the same solvent. For further purification, the product is run over a charcoal column, the fractions containing delta-9-THC are combined, concentrated and then purified by reverse phase chromatography. Again, the combined fractions containing the product are concentrated, extracted with MTBE and filtered. Ethanol is added to the filtrate and the solution is concentrated to produce an oil, from which the solvent is evaporated.

US 2015/0126596 A1 relates to methods for producing trans-(−)-delta-9-THC and trans-(+)-delta-9-THC in several different ways. In one case, the preparation is started with an enantiomeric mixture, where the two enantiomers are purified together by preparative HPLC and then crystallized as a mixture after which, in a resolving step, the (+/−)-enantiomers are separated by chiral chromatography. Another way starts also with an enantiomeric mixture, which is reacted to a nitrobenzene sulfonate, crystallized and reacted back to a clean enantiomeric mixture, which is then again separated by chiral chromatography. A further way is described, in which the two separate enantiomers are synthesized, mixed for crystallization and subsequently separated again by chiral chromatography. To purify trans-(−)-delta-9-THC by crystallization with the (+)-enantiomer and subsequent chiral separation, however, appears to be a very complicated purification method, which is bound to result in a considerable loss of material and hard to scale up in an efficient way.

Preparative HPLC is only successful on a very small scale when large losses of yield are to be avoided. Only small amounts of raw product (25 mg) can be separated into Dronabinol and the main impurity, delta-8-THC, as demonstrated in FIGS. 1a) and 1b). FIG. 1a) shows the preparative HPLC purification of 25 mg raw product obtained in the synthesis according to EP 2842933 B1, wherein the two peaks are dronabinol as main product (larger peak) and delta-8-THC as main impurity (smaller peak). FIG. 1b) shows the preparative HPLC purification of 200 mg raw product comprising dronabinol as main product and delta-8-THC as main impurity, demonstrating that these compounds can not be resolved in this quantity.

A further chromatographic purification method is super critical fluid chromatography (SFC), in which liquid $CO_2$ is used as eluant. The purification of (−)-delta-9-trans-THC by SFC is described in WO 2005/061480 A1. This process, however, requires a complex constructional setup and is very expensive. Moreover, the $CO_2$ evaporates and is lost during processing.

Further methods are derivatisations of dronabinol or precursors thereof to compounds which may be crystallized. In order to perform a crystallization, the raw product is converted into a crystallizable derivate, which is then purified by crystallization and finally converted back to dronabinol in a chemical conversion step. The most relevant methods comprise the derivatisation of delta-9-THC to suitable crystallizable salts, subsequent crystallization and thermal decarboxylation to dronabinol as described in WO 2013/045115 A1. A further option is the derivatisation of raw dronabinol to a 1-naphtoyl ester, subsequent crystallization and finally saponification to pure dronabinol (see WO 2006/007734 A1).

In summary, the methods to purify cannabinoid compounds available in the prior art are fairly complicated, time-consuming and expensive. Moreover, certain impurities derived e.g. from synthetic preparation steps, which may be structurally very similar such as isomers of the desired product, can not be removed to a satisfactory degree. This is especially true when the process is to be carried out on an economically relevant scale.

As a result, there is still a need to provide a method for the purification of cannabinoid compounds, which is suitable to achieve a maximum degree of purity while at the same time allowing purification on a large scale in an economically appropriate, i.e. a time and cost efficient way.

Simulated moving bed chromatography (SMB chromatography) is a continuous process based on the true moving bed principle, in which the solid phase moves in the opposite direction to the liquid phase and is therefore not stationary. Due to this opposing movement two pure compounds can be isolated or a pure compound can be isolated from a complex mixture.

The moving solid phase on which this concept relies, however, is technically not feasible and therefore simulated. This is implemented by arranging several preparative columns connected in series and periodically changing the valve setting so that a movement of the solid phase in the opposite direction of the flow of the liquid phase is simulated.

The system is continuously fed with a feed mixture comprising the compounds to be separated and an eluant while a raffinate and an extract are continuously withdrawn from the system. The system is therefore divided into four different separation zones, in each of which the same number of columns are distributed. The process shown in FIG. 2 comprises 8 columns in total, but alternatively, only four may be used. By periodically switching the feed, eluant, extract and raffinate ports in the same direction, each column passes through each zone once per cycle. The feed mixture is fed into the system between zones II and III, in which the actual separation occurs. Zones I and IV are regeneration zones.

The parameters, which are important for the SMB principle, are the periodical change of the position of the ports as well as the different flow rates in the four zones. These four flow rates are regulated by four pumps. The extract pump in zone II and the raffinate pump in zone IV are inside the column circle, the eluant and the feed pump are located outside of the column circle. A fine regulation is achieved by two needle valves, which regulate the ratio between the circle flow and the outlet flow.

While the prior art does not provide a process for the purification of cannabinoid compounds, which is suitable to achieve a purity level comparable to the process according to the present invention as described below, in particular when performed at a preparative scale, it has now been found out, that the purification of cannabinoid compounds using a simulated moving bed chromatographic system, preferably in combination with one or more additional extraction step(s), provides one or two desired cannabinoid products with an unexpectedly high degree of purity while still allowing the process to be implemented on an economically relevant scale.

This finding was unexpected as conventional silica gel chromatography of larger amounts of dronabinol fails to provide a viable option to separate the product from its isomers, while it is on the other hand not feasible to scale up reversed phase HPLC chromatography to preparative significant amounts. The method according to the invention, however, surprisingly compensates both theses problems and provides a way to obtain pure product on a large scale.

It was therefore an objective of the present invention to provide a purification method which overcomes the above mentioned problems.

In particular, it was an objective of the present invention to provide a purification process for one or two cannabinoid compound(s) from a reaction mixture derived from a synthetic preparation process, especially a process as described in EP 2842933 B1.

It was also an object of the present invention to obtain the desired cannabinoid compound(s) in a degree of purity that any of its/their isomers are below a detection level and furthermore in enantiopure form.

The objectives given above are met by a method for purifying one or two cannabinoid compounds comprising the steps:
i) providing a mixture comprising at least one cannabinoid compound obtained by enantiopure synthesis and one or more of its isomers and optionally one or more further organic compounds, and
ii) simultaneously,
  a) continuously feeding the mixture of step i) through a feed port into a simulated moving bed chromatographic apparatus comprising at least four columns connected in series and containing a stationary phase, and
  b) continuously feeding eluant into the apparatus through an eluant port, and
  c) continuously withdrawing the extract through an extract port, and
  d) continuously withdrawing the raffinate through a raffinate port,
wherein the extract and/or the raffinate respectively comprise(s) one purified cannabinoid compound and wherein the extract and/or the raffinate comprising one purified cannabinoid compound comprise(s) less than 100 ppm, preferably less than 70 ppm, particularly preferably less than 50 ppm in total of any isomer(s) of the purified cannabinoid compound present in step i).

As described above, SMB chromatography allows separation and purification of one or simultaneously two desired product compounds, the stronger adsorbing compound is obtained as the extract and the weaker adsorbing compound is obtained as the raffinate. Advantageously, a mixture comprising at least one cannabinoid compound together with at least one of its isomers, such as a reaction mixture from a synthesis step, may be subjected to the method according to the invention to provide highly pure products in large yields. The at least one cannabinoid compound and its isomer(s) present in the mixture provided in step i) are likely very similar in chemical structure and therefore also in their physical properties. Consequently, they are particularly hard to separate. Using the method according to the present invention, however, the cannabinoid compound(s) can efficiently be separated from their isomers.

The one or more further organic compound(s) present in the mixture provided in step i) may be any compound(s) selected from synthetic starting materials or side products of the synthesis, which are not cannabinoid compounds.

As the steps a) to d) are carried out simultaneously and continuously, the process is very time efficient and the required amount of eluant is significantly reduced compared to conventional chromatography. Additionally, it is advantageous that the solid phase can be used for separation during the entire process. This increases the efficiency of the separation and simultaneously reduces the required amount of eluant. Once the adsorption equilibrium is reached, the composition of the raffinate and extract do not change anymore as long as the respective parameters are not changed. The loss of valuable materials is reduced to <5%.

As a simulated moving bed chromatographic apparatus, any system suitable to perform simulated moving bed chromatography may be used. The stationary or solid phase may be any material, which the skilled person can easily choose according to the nature of the mixture and the compounds to be separated. To determine the respective flow rates at the different pumps, several methods and models are known in the prior art which may be implemented in order to achieve an optimal separation of the desired compound(s).

The desired compound(s) is/are obtained in the extract and/or the raffinate in a degree of purity with respect to any isomer of the desired cannabinoid compound(s), which is preferably below detection limit, in particular the total amount of any isomer of the cannabinoid compound(s) which was/were present in step i) is less than 100 ppm, preferably less than 70 ppm and particularly preferably less than 50 ppm. The degree of purity may be determined chromatographically using an HPLC apparatus (e.g. Knauer HPLC smartline series) and the appropriate USP reference standards for dronabinol and its isomers. A Restek—Raptor (ARC—18, 2.7 mm, 150×4.6 mm) HPLC column may be used together with the respective USP eluent (45% methanol, 25% water, 20% tetrahydrofuran, 10% acetonitrile) with an eluent flow of 0.8 mL/min.

According to a further aspect the method as described above additionally comprises the step
iii) subjecting the extract and/or the raffinate comprising one purified cannabinoid compound to one, two or more further extraction step(s), preferably using an oil as the extracting agent,
wherein the extract and/or the raffinate respectively obtained in step iii) comprise(s) one purified cannabinoid compound and less than 100 ppm, preferably less than 70 ppm, particularly preferably less than 50 ppm in total of any further organic compound(s) present in step i).

By subjecting the desired cannabinoid compound(s) which is/are contained in the extract and/or the raffinate to one or more further extraction step(s), impurities other than the isomers present in step i) can be removed. In particular, organic compounds, which may be present from the synthetic step such as starting materials or side products of the synthesis can be removed to a degree such that they are present in an total amount of less than 100 ppm, preferably less than 70 ppm, particularly preferably less than 50 ppm.

The extraction agent may be any substance selected from the group consisting of cyclohexane, heptane and other oxygen free hydrocarbons.

Suitable oils to be used as extracting agents are selected from the group consisting of plant oils with medium chain triglycerides, preferably containing the fatty acids capric acid and caprylic acid. Advantageously, when using an oil as extracting agent, the resulting product comprising the desired cannabinoid compound—besides being highly pure—is particularly stable when kept under argon and in the dark. In particular, the medium chain triglycerides mentioned above provide an antioxidant effect and therefore enhance the stability of the product.

In the method according to the invention, the cannabinoid compound(s) to be purified may be selected from the group consisting of cannabidiol, trans-(−)-delta-9-tetrahydrocannabinol, cannabidivarin, trans-(−)-delta-9-tetrahydrocannabivarin and cannabigerol.

Any of these compounds may be obtained by chemical synthesis as described in the prior art, which results in reaction mixtures comprising one or more cannabinoid compounds such as the desired product and its synthetic precursors, as well as at least one isomer of the product compound(s) and further organic compounds such as starting materials or side products of the synthesis, which are not cannabinoid compounds. These mixtures can be purified to a high degree and with good yields on a large scale by the method according to the present invention.

In a particularly preferred embodiment, the method according to the invention is used to purify the reaction product(s) of the synthesis steps described in EP 2842933 B1. The reaction product(s) to be purified are preferably trans-(−)-delta-9-THC (III) or cannabidiol (II).

According to one aspect, in the method according to the present invention step i) includes the following step:
  conversion of menthadienol with an olivetolic acid ester to a cannabidiolic acid ester of formula (IX)

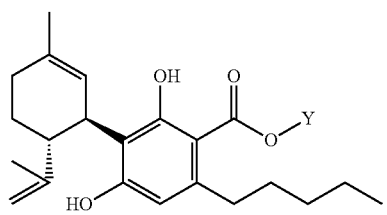

(IX)

wherein Y is an organic residue,
preferably in a continuous process.

According to a further aspect, step i) comprises the conversion of a cannabidiolic acid ester of formula (IX), wherein Y is an organic residue with an alcohol of the formula HO-X,
  wherein
  X is an aliphatic residue with one, two, three or more than three hydroxyl groups, wherein the total number of C-atoms in the aliphatic residue X is not greater than 15, and
  wherein the aliphatic residue is
    saturated or unsaturated
    and
    branched or unbranched,
  wherein Y is different from X and selected such that the alcohol of formula HO-Y, which is generated during the conversion, boils at a lower temperature at 1013 hPa than the used alcohol of formula HO-X.

According to yet another aspect of the method according to the invention, the compound generated by the conversion of the cannabidiolic acid ester of formula (IX) with the alcohol of formula HO-X is treated in such a way that it is decarboxylated and saponified to generate cannabidiol (II).

In a further aspect of the method according to the invention, the cannabidiol, which is present after the decarboxylating saponification, is cyclised to trans-(−)-delta-9-tetrahydrocannabinol (III), preferably in the absence of halogenated solvents.

In the synthesis of delta-9-tetrahydrocannabinol according to EP 2842933 B1, an impurity which is very hard to remove is olivetol, which is generated during the synthesis.

Surprisingly, when the method according to the present invention is used to purify the product delta-9-THC in combination with the one or more further extraction step(s), any residual olivetol can be removed to such a degree that it is no more detectable by conventional HPLC analysis as demonstrated in example 3.

Therefore the present invention particularly relates to a method as described above, wherein the one or one of the further organic compound(s) present in step i) is olivetol.

Furthermore, as already mentioned in the introduction, the raw product generated by the synthesis according to EP 2842933 B1 has a delta-9-THC content of 65-75%, as well as 20-30% of the isomer delta-8-tetrahydrocannabinol as main impurity. Furthermore, delta-9(11)-tetrahydrocannabinol may be present. Due to the structural similarity of the isomers, the desired delta-9-THC is very hard to purify from this reaction mixture.

Using the method according to the present invention, however, a purity may be obtained such that these isomers can no more be detected in the product as demonstrated in example 3.

Therefore in a particularly preferred embodiment, in the method according to the invention, the mixture provided in step i) comprises trans-(−)-delta-9-tetrahydrocannabinol together with delta-8-tetrahydrocannabinol and/or delta-9(11)-tetrahydrocannabinol.

According to a further preferred embodiment, the method according to the invention is used to purify the reaction product(s) of the synthesis steps described in European patent application EP 15156750.0. The reaction product(s) to be purified are preferably cannabidivarin (VII) or trans-(−)-delta-9-tetrahydrocannabivarin (VIII).

According to one aspect in the method according to the present invention, step i) comprises the conversion of menthadienol of formula (I) with a divarinic acid ester of formula (IV), to an ester of formula (V),

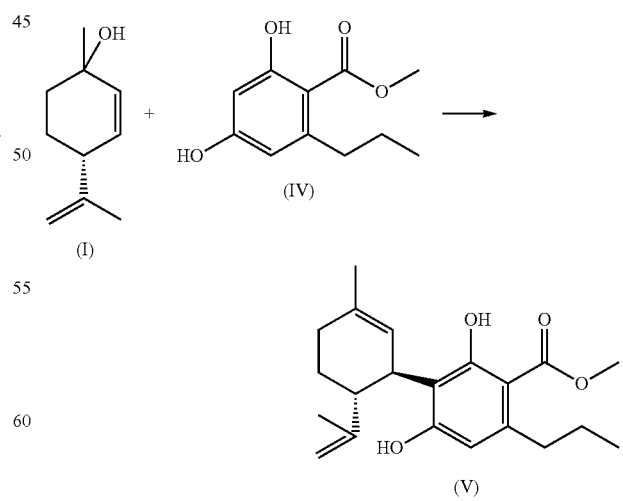

According to a further aspect, in the method according to the invention, step i) comprises the transesterification of the ester of formula (V)

with an alcohol of the formula HO-X,
wherein
X is an aliphatic residue with no, one, two, three or more than three hydroxyl groups, wherein the total number of C-atoms in the aliphatic residue X is not greater than 15, and
wherein the aliphatic residue is
saturated or unsaturated
and
branched or unbranched,
acyclic or cyclic,
with the proviso that the alcohol of formula HO-X is selected from the group consisting of cyclohexanol and hexanol in case X is an aliphatic residue with no hydroxyl group.

According to yet a further aspect, in the method according to the invention, the compound generated by the conversion of ester of formula (V) with the alcohol of formula HO-X is treated in such a way that it is decarboxylated and saponified to generate cannabidivarin (VII).

In a further aspect of the method according to the invention, the cannabidivarin, which is present after the decarboxylating saponification, is cyclised to trans-(−)-delta-9-tetrahydrocannabivarin (VIII), preferably in the absence of halogenated solvents.

The reaction products of the synthesis steps as described in European patent application EP 15156750.0, may be purified by the method according to the invention. The advantages described above in the context of the purification of the synthesis product(s) according to EP 2842933 apply accordingly.

Finally, the present invention also relates to an extract or raffinate obtained or obtainable in step c) or d) of a method as described above, or an extract or raffinate obtained or obtainable in step iii) of a method as described in the context of the corresponding embodiment above.

An extract or raffinate obtained or obtainable in step c) or d) of a method as described above, or an extract or raffinate obtained or obtainable in step iii) of a method as described in the context of the corresponding embodiment above, comprises the desired cannabinoid compound in a degree of purity, in particular with respect to its isomers, which could not be achieved by any of the conventional processes available in the prior art.

The following examples describe particular embodiments of the present invention, without meaning to limit the scope of protection.

EXAMPLE 1: SYNTHESIS OF DELTA-9-THC

Step 1: Coupling Step (in the Continuous Process); Synthesis of Cannabidiolic Acid Methyl Ester (I)

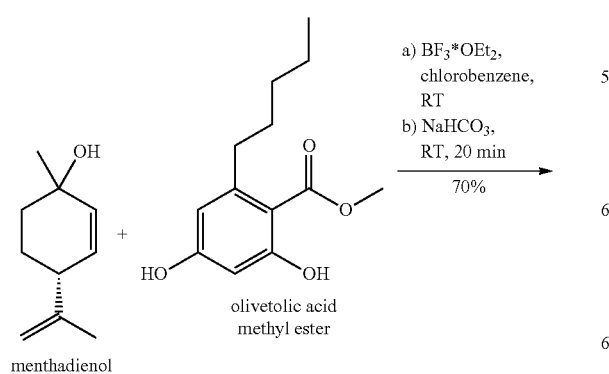

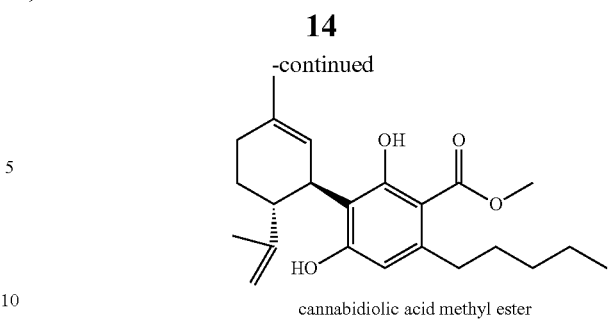

cannabidiolic acid methyl ester 300 g (2.0 mol) menthadienol and 476 g (2.0 mol) olivetolic acid ester are dissolved at ca. 22° C. in 1,370 g of chlorobenzene (2,000 mL solution A), likewise 94 g (0.66 mol) boron trifluoride*etherate are dissolved in 640 g of chlorobenzene at ca. 22° C. (666 mL solution B), Solution A at a flow rate of 72 mL/min and solution B at a flow rate of 24 mL/min are pumped into a stirred reaction chamber via two separate dosing pumps, from the reaction chamber the reaction composition runs via a PTFE hose into a stirred solution of 1,000 g of sodium bicarbonate. The total reaction time is ca. 20 min. After termination of the metering the hydrolyzed reaction solution is stirred for a further 30 min.

Then the hydrolyzed reaction solution is transferred into a 5 L jacket reaction vessel, the aqueous phase is separated and the solvent chlorobenzene is removed in vacuo. Ca. 2,000 g of toluene are added to the remaining 730 g of raw material and the unreacted olivetolic acid ester is extracted through the addition of 1,200 g 1% aqueous sodium hydroxide solution (four times). After acidifying with semi conc. sulfuric acid and re-extraction of this aqueous phase, ca. 30% (140 g) of non converted olivetolic acid ester are recovered.

There are ca. 520 g of cannabidiolic acid methyl ester in the toluene phase, which corresponds to a theoretical yield of ca. 70%. This first intermediate serves as starting material for the following transesterification.

Step 2: Transesterification, Synthesis of 2-hydroxyethyl Cannabidiolate:

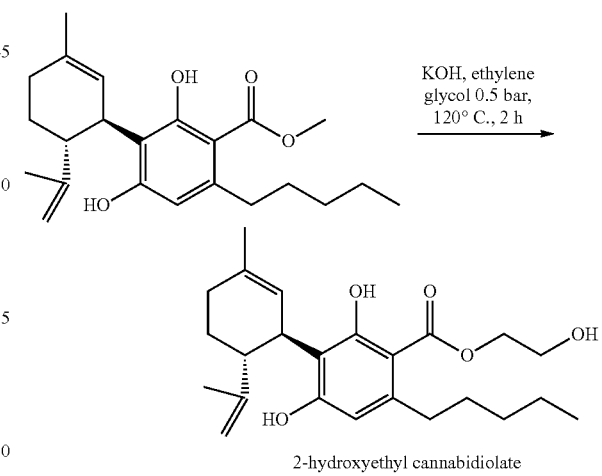

2-hydroxyethyl cannabidiolate

The toluene is removed in vacuo and to the remaining first intermediate 600 g of ethylene glycol are added under stirring followed by a solution of 85 g of potassium hydroxide in 300 g ethylene glycol. A vacuum of ca. 0.5 bar is applied and it is heated to 120° C. for 2 h, whereby ca. 40 g of methanol distill off. The resulting product composition mainly comprises 2-hydroxyethyl cannabidiolate.

Step 3: Saponification/Decarboxylation, Synthesis of Cannabidiol (X):

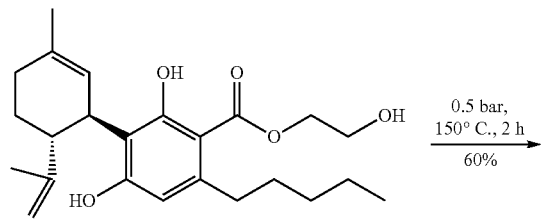

cannabidiol

Subsequently, the temperature is increased to 150° C. and it is stirred at this temperature for 2 h. The product composition resulting from the transesterification comprising mainly 2-hydroxyethyl cannabidiolate is cooled down to ca. 40° C. and 500 g of water as well as 500 g of n-heptane are added and ca. 150 g of semi conc. sulfuric acid are added for neutralization. After phase separation, the solvent is removed using a rotary evaporator and the remainder is distilled over a thin-film evaporator using a vacuum of ca. 0.5 mbar and a jacket temperature of 230° C. 310 g of cannabidiol are obtained in the form of a viscous, yellowish oil with a purity of 85%, which corresponds to a theoretical yield of 60% in relation to the used cannabidiolic acid ester.

This viscous, yellowish oil is then recrystallized in ca. 200 g of n-heptane at ca. −5° C., after which 210 g of white crystallizate with a purity of 99% cannabidiol are obtained.

Step 4: Cyclization, Synthesis of Delta-9-THC:

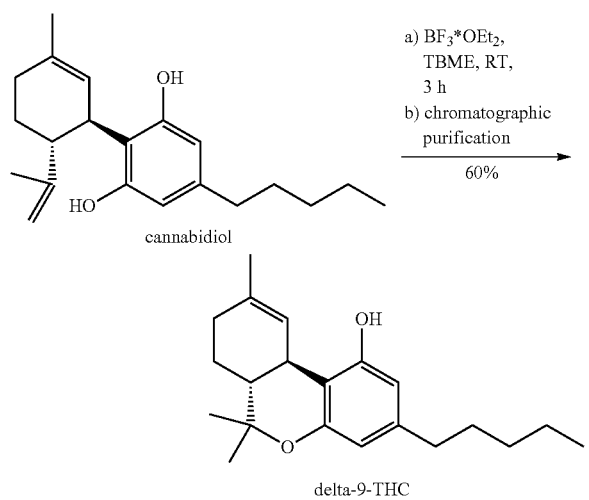

50 g of pure cannabidiol are dissolved in 250 g methyl-tert-butylether and 40 g of boron trifluoride*acetic acid complex are added under stirring within 10 min at ca. 22° C. It is stirred for 3 h at said temperature and then 200 g of ice water are added, the organic phase is washed with sodium bicarbonate solution and the solvent is removed using a rotary evaporator. The remaining raw material of ca. 50 g contains 74% trans-(−)-delta-9-tetrahydrocannabinol (delta-9-THC), 25% of side products as well as <1% cannabidiol.

EXAMPLE 2: SYNTHESIS OF CANNABIDIVARIN AND TETRAHYDROCANNABIVARIN

Step 1: Coupling Step

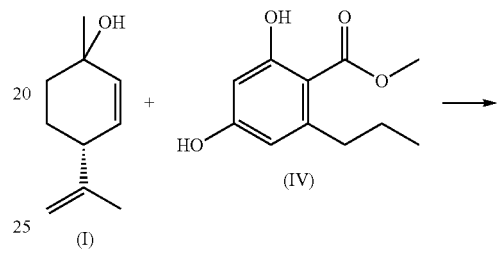

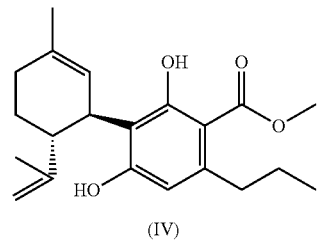

273 g (1.8 Mol) menthadienol and 377 g (1.8 Mol) divarinic acid methylester are dissolved at RT in 1.450 g toluene (2.300 mL solution A), likewise, an adequate amount of borontrifluoride*etherate are dissolved in 540 g toluene at RT (710 mL solution B). Solution A and solution B are pumped into a stirred reaction chamber via two separate dosing pumps, from the reaction chamber the reaction composition runs via a PTFE hose into a stirred solution of 1,000 g of sodium bicarbonate. The total reaction time is about 25 mins. After termination of the metering the hydrolyzed reaction solution is stirred for about 1 hour.

Then the hydrolyzed reaction solution is transferred into a 5 L jacket reaction vessel, the aqueous phase is separated. The not reacted divarinic acid ester is extracted by six times adding 1.000 g of 1% aqueous sodium hydroxide solution. After acidifying with semi conc. sulfuric acid and re-extraction of this aqueous phase, ca. 30% (130 g) of non converted divarinic acid ester are recovered. In the toluene phase, about 320 g cannabidivarinic acid methylester (V) are contained, which corresponds to a theoretical yield of 50%. This first intermediate serves as starting material for the following transesterification.

Step 2: Transesterification Step:

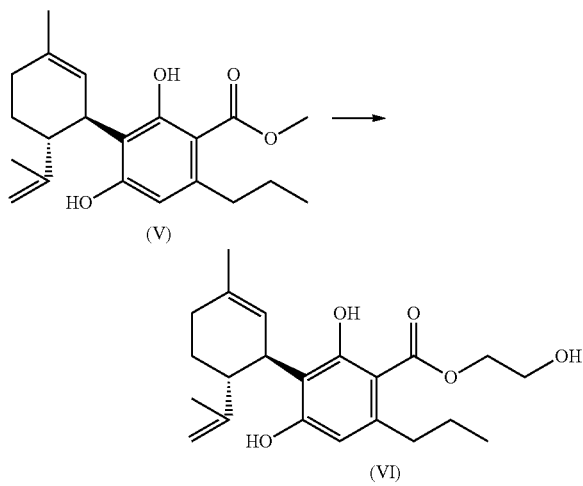

The toluene is removed in vacuo and to the remaining first intermediate 650 g of ethylene glycol are added under stirring followed by a solution of 122 g of potassium hydroxide in 420 g ethylene glycol. A vacuum of ca. 0.5 bar is applied and it is heated to 100-120° C. for 2 h, whereby ca. 40 g of methanol distill off. The resulting product composition mainly comprises 2-hydroxy-ethyl-cannabidivarinolat (VI).

Step 3: Saponification/Decarboxylation:

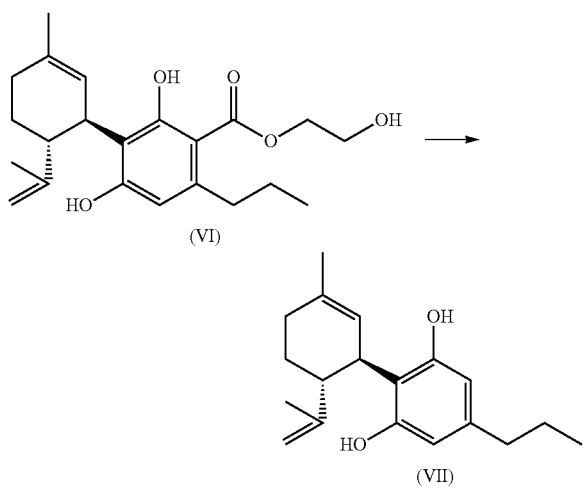

Subsequently, the temperature is increased to 150° C. and it is stirred at this temperature for 3-4 h (also in vacuo; cfl. step 2). The product composition resulting from the transesterification is cooled down to ca. 40° C. and 1.500 g of water as well as 800 g of methyl-tert. butyether are added and ca. 180 g of semi conc. sulfuric acid are added for neutralization. After phase separation, the solvent is removed using a rotary evaporator and the remainder is distilled over a thin-film evaporator using a vacuum of ca. 1 mbar and a jacket temperature of 230° C. 270 g of cannabidivarin (VII) are obtained in the form of a viscous, yellowish oil with a purity of 85%, which corresponds to a theoretical yield of 85% in relation to the used cannabivarinic acid ester.

This viscous, yellowish oil is then recrystallized in ca. 270 g of n-heptane at ca. 10° C., after which 190 g of white to lightly yellow crystallizate with a purity of 99% cannabidivarin (VII) are obtained.

Step 4: Cyclization to Tetrahydrocannabivarin (THCV):

50 g of pure cannabidivarin (VII) are dissolved in 250 g methylene chloride and 40 g of boron trifluoride*ether complex are added under stirring within 10 min at ca. 22° C. It is stirred for 20 mins at said temperature and then 200 g of ice water are added, the organic phase is washed with sodium bicarbonate solution and the solvent is removed using a rotary evaporator. The remaining raw material of ca. 50 g contains 74% trans-(−)-delta-9-tetrahydrocannabivarin (VIII) and 26% of side products.

EXAMPLE 3: PURIFICATION OF A RAW PRODUCT AS OBTAINED IN EXAMPLE 1

Any steps described herein were conducted in an inert gas atmosphere (argon) due to the air-sensitivity of the dronabinol. After processing the reaction mixture, the following composition of the raw product is obtained:

HPLC-Analysis: (DAD, in Area-%)

| | batch number | | |
|---|---|---|---|
| substance | LN 703795 | LN 703814 | LN 703842 |
| olivetol (2.8 min) | 1.2% | 1.3% | 1.2% |
| cannabidiol (8.5 min) | 0.3% | 0.4% | 0.4% |
| dronabinol (14.8 min) | 71.6% | 71.4% | 72.1% |
| Δ9(11)-tetrahydrocannabinol (15.6 min) | 0.4% | 0.4% | 0.4% |
| Δ8-tetrahydrocannabinol (17.0 min) | 26.3% | 26.3% | 25.4% |

FIG. 3 shows the exemplary chromatogram of LN 703795.

The chromatographic system is based on a known SMB apparatus of the company Knauer (Germany). The system comprises 8 separation columns (Knauer Vertex Plus, 250×8 mm), as well as the required pumps. The column configuration corresponds to the standard 2-2-2-2 arrangement. The movement of the individual columns is implemented by a 64 port rotary valve. The switching time of the valve is 10.81 seconds. The valve and the HPLC columns are located in a tempered column oven. The temperature of the chromatographic system is 20 to 60° C., preferably 30° C.

A solid phase suitable for the separation is an RP material (Eurospher II silica gel, C18P) with a grain size of 10 to 100 μm, preferably 20 to 45 μm. The solid phase showed no signs of deterioration over a time period of two years. This is a further advantage compared to classical chromatographic systems.

As mobile (liquid) phase/eluant a mixture of methanol, tetrahydrofuran and water is used, preferably with the composition: methanol (62%), tetrahydofuran (17%), water (21%). Furthermore, 0.01% ascorbic acid is added to the mixture as antioxidant.

The feed mixture comprises the above described raw product dissolved in eluant mixture at a concentration of 12.5 g/L. The eluant, extract and raffinate pump each have a maximum flow rate of 50 ml/min, the feed pump a maximum flow rate of 10 ml/min. In the process described herein, the following flow rates are used: eluant pump (zone 1; 4.4 ml/min), extract pump (zone 2, 3.2 ml/min), raffinate pump (zone 4, 1.3 ml/min) and feed pump (zone 3, 0.2 ml/min). The flow rates are measured with a Humonics Optiflow 520.

The supply of the system with eluant and feed solution is done from suitable stock containers, which are secured for fire safety. Eluant and feed solution are periodically overlaid with argon to keep oxygen from the air out. Before entering the system, eluant and feed solution are pumped though a deaerator.

The SMB process does not need a constant supervision. The process described herein may be run continuously over several weeks without changing the parameters and without having a change in the yield. The particular stability of the process allows a 24 hour operation, without needing shift workers. Internal controls of the process are performed once a day.

With the process described herein, 0.15 g/hour of dronabinol can continuously be obtained from the raffinate. This corresponds to a daily rate of 3.6 g.

By upscaling the process from 8 mm to 50 mm columns, the daily yield can be increased to 144 g of pure dronabinol. This corresponds to a yearly production of about 40 kg of dronabinol.

The raffinate derived from the SMB process has the following composition:

HPLC-Analysis: Raffinate (DAD, in Area-%)

| | batch number | | |
|---|---|---|---|
| substance | LN 703795 | LN 703814 | LN 703842 |
| olivetol | 1.1% | 1.1% | 1.4% |
| cannabidiol | 0.4% | 0.2% | 0.4% |
| dronabinol | >97% | >97% | >97% |
| Δ9(11)-tetrahydrocannabinol | n.d. | n.d. | n.d. |
| Δ8-tetrahydrocannabinol | n.d. | n.d. | n.d. | n.d. = not detectable

FIG. 4 shows the exemplary chromatogram of the raffinate from LN 703795.

After adjusting the adsorption equilibrium, the obtained raffinate is subjected to further processing. The solvent is reduced by distillation (100 mbar vacuum at a temperature of 30° C.) to 30% organic. The distilled solvent is reintroduced to the process as eluant after adjustment of the starting mixture. The obtained reduced raffinate is extracted twice with cyclohexane (50 wt.-% with respect to the reduced raffinate). The olivetol contained in the raffinate stays in the water/organic phase, while the dronabinol passes into the cyclohexane phase. After removal of the solvent by distillation, dronabinol is obtained with a content of >99% at a residual solvent content of below 100 ppm.

HPLC-Analysis: Final Product (DAD, in Area-%)

| | batch number | | |
|---|---|---|---|
| substance | LN 703795 | LN 703814 | LN 703842 |
| olivetol | n.d. | n.d. | n.d. |
| cannabidiol | 0.31% | 0.51% | 0.41% |
| dronabinol | 99.34% | 98.10% | 99.15% |
| Δ9(11)-tetrahydrocannabinol | n.d. | n.d. | n.d. |
| Δ8-tetrahydrocannabinol | n.d. | n.d. | n.d. | n.d. = not detectable

FIG. 5 shows the exemplary chromatogram of the final product from LN 703795.

For extraction, instead of cyclohexane, a plant oil based on a mixture of medium chain triglyceride may alternatively be used. This leads to a comparable purity as obtained with cyclohexane and a stable storage medium for the pure compound.

SHORT DESCRIPTION OF THE DRAWINGS

FIG. 1a) shows the preparative HPLC purification of 25 mg raw product obtained in the synthesis according to EP 2842933 B1, wherein the two peaks are dronabinol as main product (larger peak) and delta-8-THC as main impurity (smaller peak).

FIG. 1b) shows the preparative HPLC purification of 200 mg raw product obtained in the synthesis according to EP 2842933 B1 comprising dronabinol as main product and delta-8-THC as main impurity, which can not be resolved in this quantity.

FIGS. 2a) and b) show a schematic setup of a SMB system.

Figure 1A:
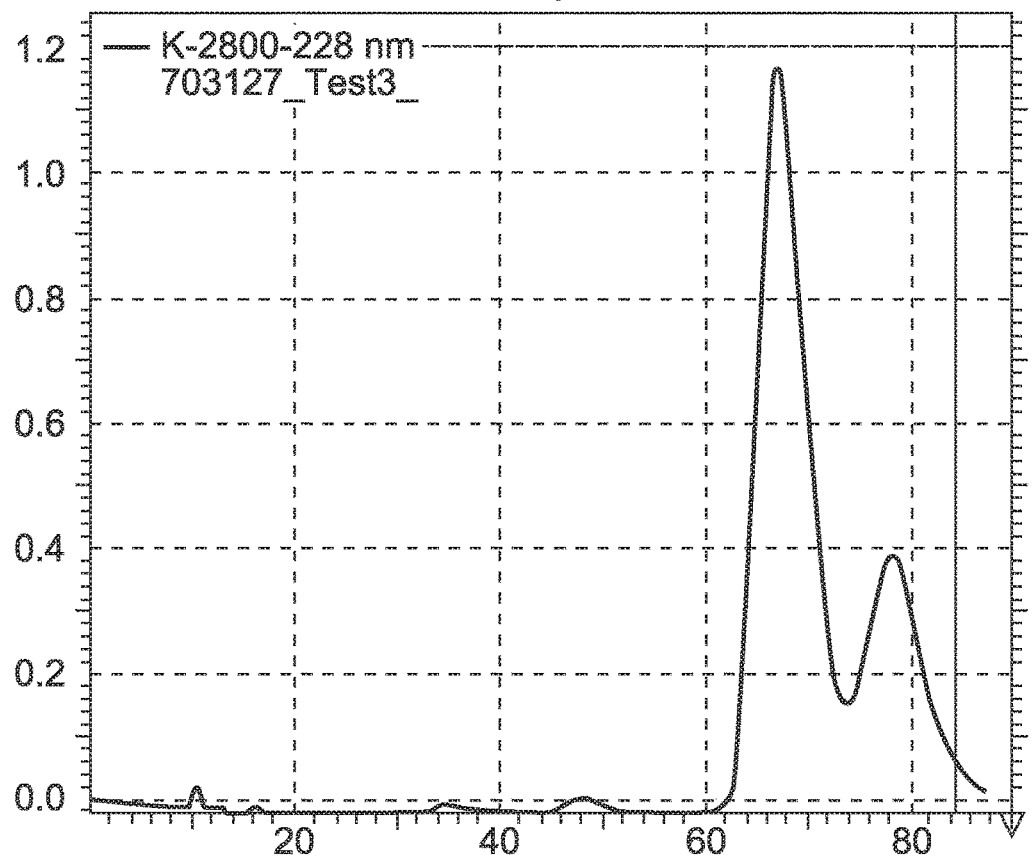
Figure 1B:
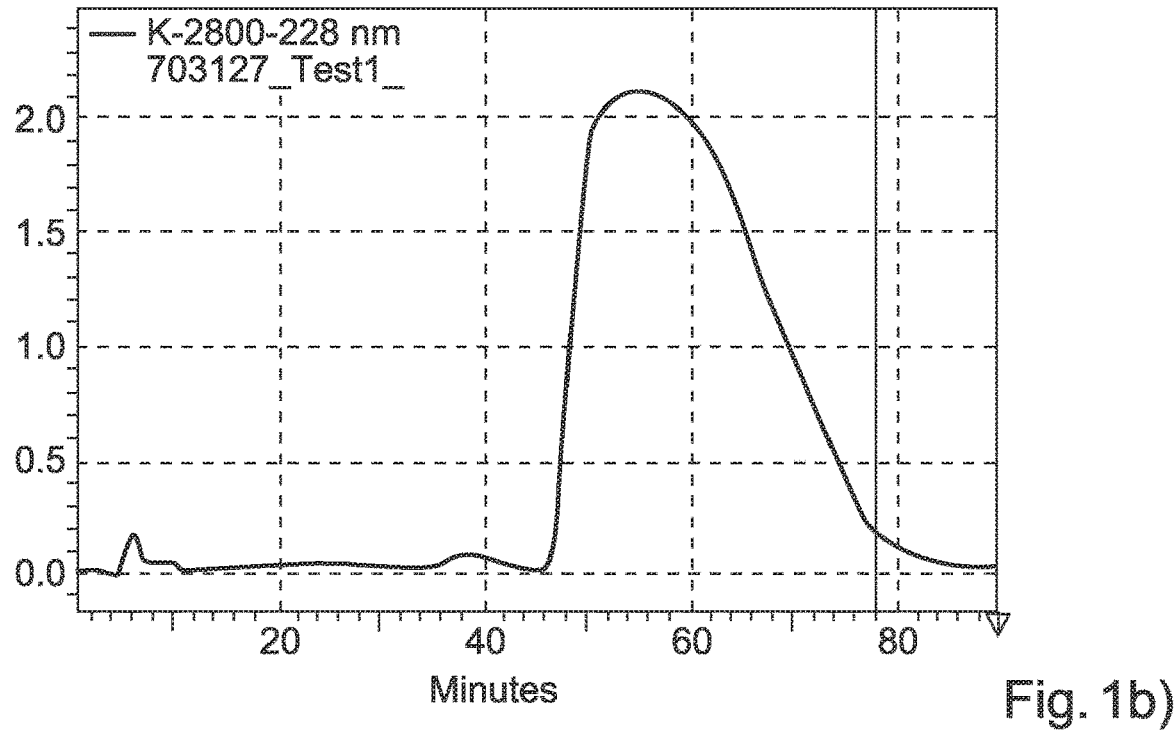
Figure 2A:
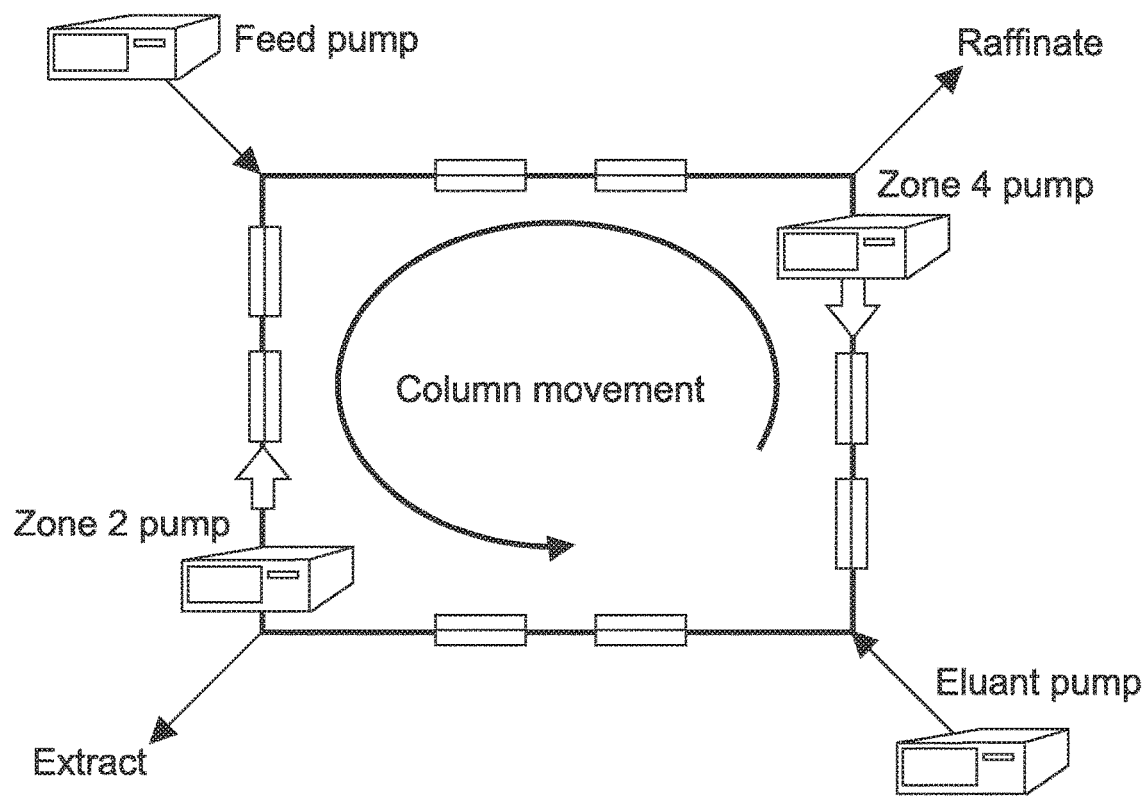
Figure 2B:
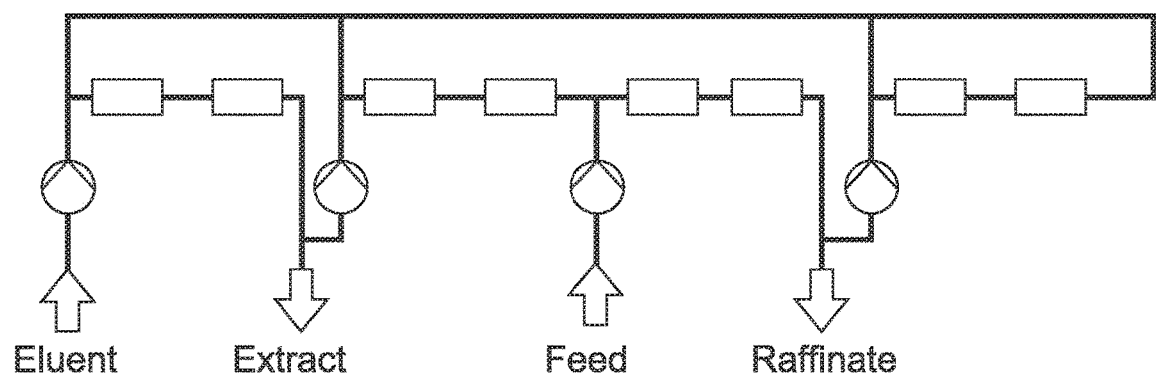
Figure 3:
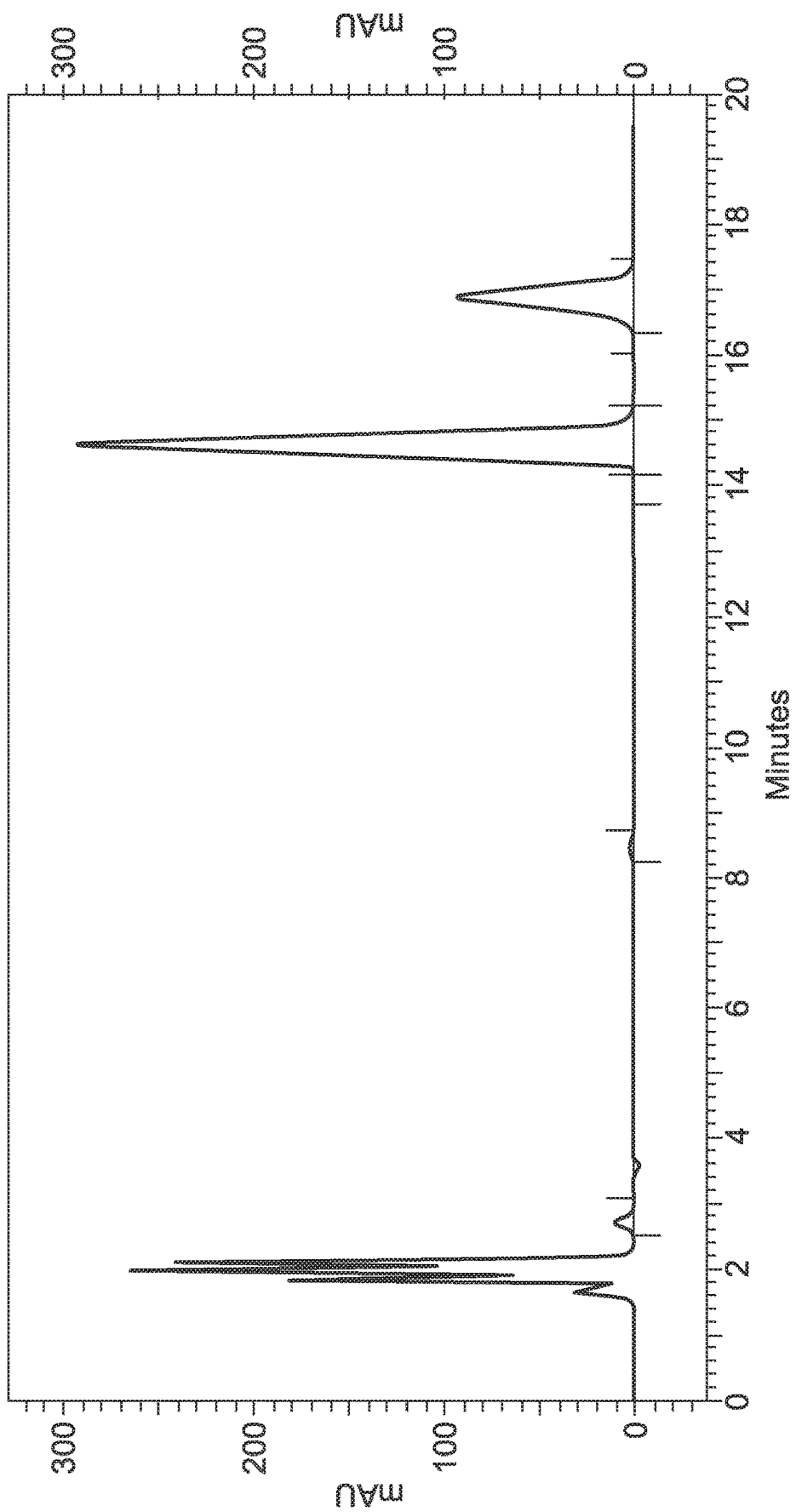
FIG. 3 shows the exemplary chromatogram of LN 703795.
Figure 4:
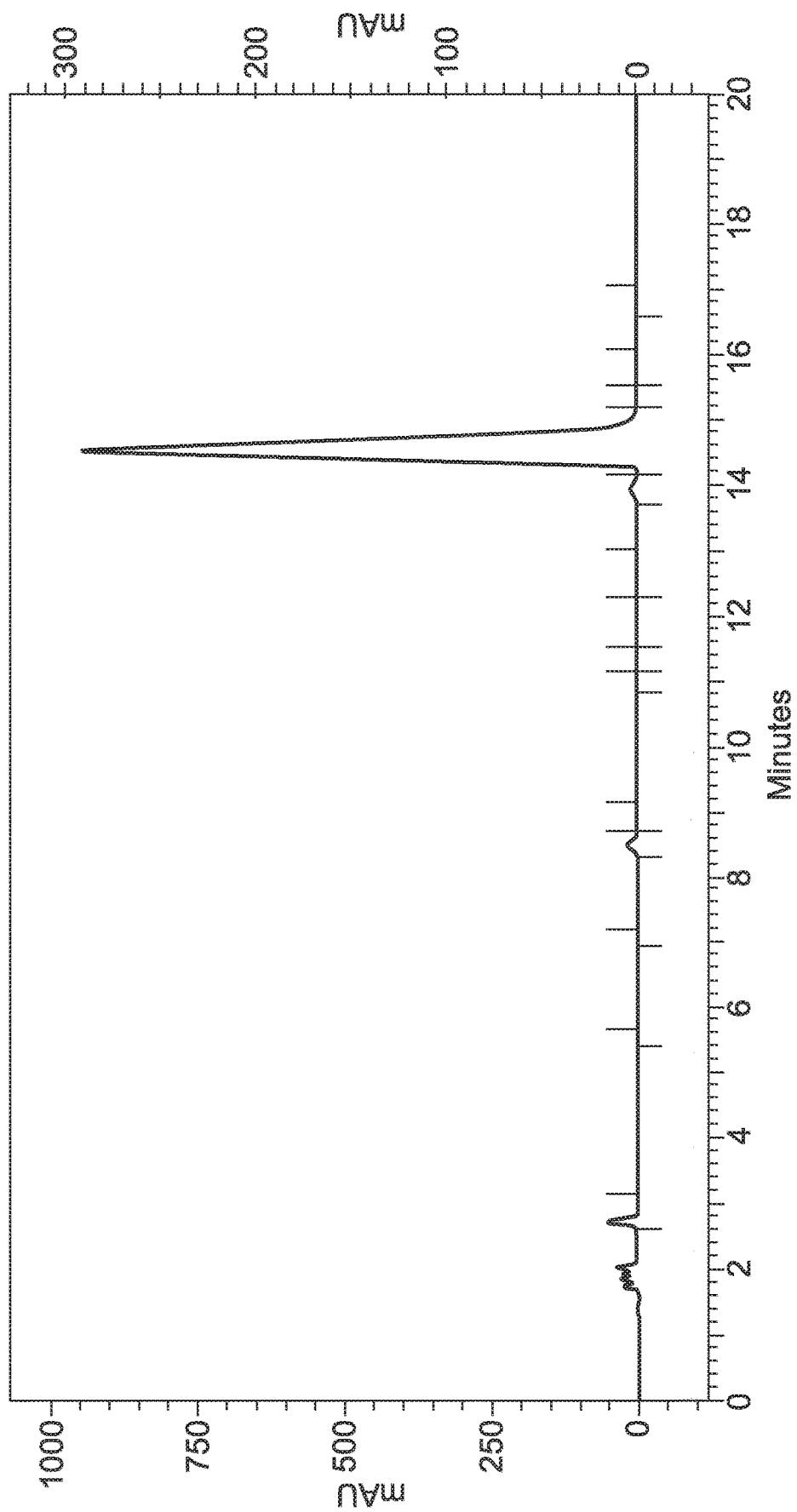
FIG. 4 shows the exemplary chromatogram of the raffinate from LN 703795.
Figure 5:
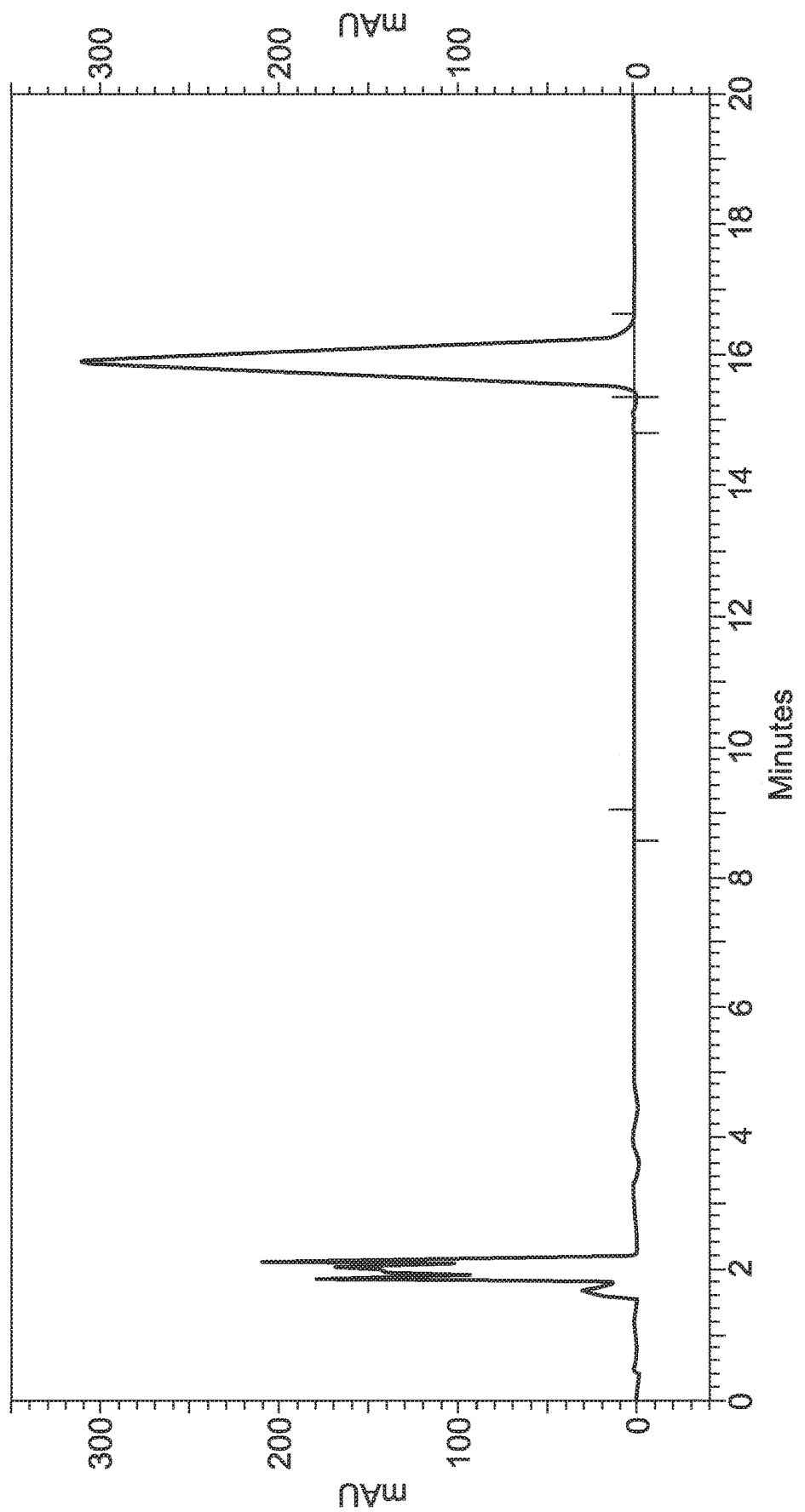
FIG. 5 shows the exemplary chromatogram of the final product from LN 703795.

The invention claimed is:

1. A method for purifying a cannabinoid compound obtained by enantiopure synthesis, wherein the cannabinoid compound is cannabidiol, trans-(−)-delta-9-tetrahydrocannabinol, cannabidivarin, trans-(−)-delta-9-tetrahydrocannabivarin, or cannabigerol, the method comprising:
   i) providing a mixture comprising the cannabinoid compound obtained by enantiopure synthesis and one or more of its isomers and optionally one or more further organic compounds, and
   ii) simultaneously,
      a) continuously feeding the mixture of step i) through a feed port into a simulated moving bed chromatographic apparatus comprising at least four columns connected in series and containing a stationary phase, and
      b) continuously feeding eluant into the apparatus through an eluant port, and
      c) continuously withdrawing the extract through an extract port, and
      d) continuously withdrawing the raffinate through a raffinate port,
         wherein the extract and/or the raffinate respectively comprises the purified cannabinoid compound and less than 100 ppm in total of any isomer(s) of the purified cannabinoid compound present in step i).

2. The method according to claim 1, additionally comprising:
   iii) subjecting the extract and/or the raffinate comprising one the purified cannabinoid compound to one, two or more further extraction step(s), wherein the extract and/or the raffinate respectively obtained in step iii) comprise(s) the purified cannabinoid compound and less than 100 ppm in total of any further organic compound(s) present in step i).

3. The method according to claim 1, wherein the cannabinoid compound is trans-(−)-delta-9-tetrahydrocannabinol or trans-(−)-delta-9-tetrahydrocannabivarin.

4. The method according to claim 1, wherein step i) includes conversion of menthadienol with an olivetolic acid ester to a cannabidiolic acid ester of formula (IX)

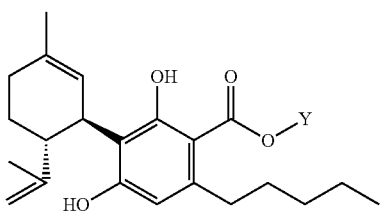

wherein Y is an organic residue.

5. The method according to claim 4, wherein step i) comprises the conversion of a cannabidiolic acid ester of formula (IX), wherein Y is an organic residue, with an alcohol of the formula HO-X, wherein X is an aliphatic residue with one, two, three or more than three hydroxyl groups and the total number of C-atoms in the aliphatic residue X is not greater than 15, wherein Y is different from X and selected such that the alcohol of formula HO-Y, which is generated during the conversion, boils at a lower temperature at 1013 hPa than the alcohol of formula HO-X.

6. The method according to claim 5, wherein the compound generated by the conversion of the cannabidiolic acid ester of formula (IX) with the alcohol of formula HO-X is decarboxylated and saponified to generate cannabidiol of formula (II)

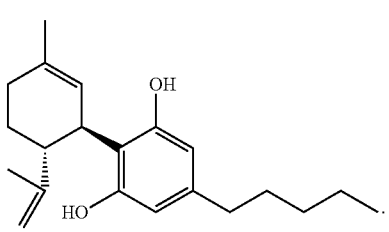

7. The method according to claim 6, wherein the cannabidiol, which is present after the decarboxylating saponification, is cyclised to trans-(−)-delta-9-tetrahydrocannabinol of formula (III)

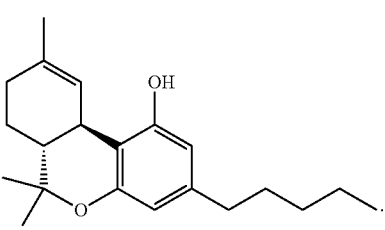

8. The method according to claim 4, wherein the mixture comprising the cannabinoid compound in step i) comprises the one or more further organic compound(s), and the one or more further organic compound(s) comprises olivetol.

9. The method according to claim 7, wherein the mixture provided in step i) comprises trans-(−)-delta-9-tetrahydrocannabinol together with delta-8-tetrahydrocannabinol and/or delta-9(11)-tetrahydrocannabinol.

10. The method according to claim 1, wherein step i) comprises the conversion of menthadienol of formula (I) with a divarinic acid ester of formula (IV), to an ester of formula (V),

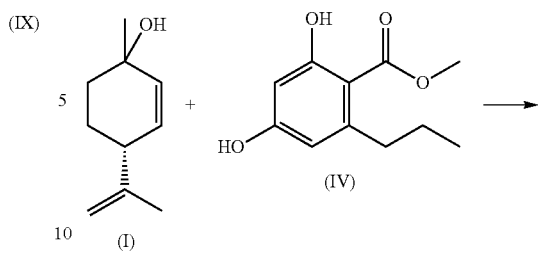

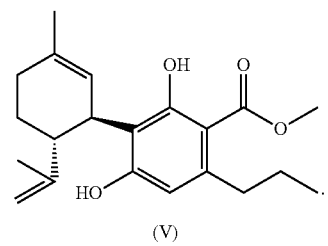

11. The method according to claim 10, wherein step i) comprises the transesterification of the ester of formula (V) with an alcohol of the formula HO-X, wherein X is an aliphatic residue with no, one, two, three or more than three hydroxyl groups, wherein the total number of C-atoms in the aliphatic residue X is not greater than 15, with the proviso that the alcohol of formula HO-X is selected from the group consisting of cyclohexanol and hexanol in case X is an aliphatic residue with no hydroxyl group.

12. The method according to claim 10, wherein the compound generated by the conversion of the ester of formula (V) with the alcohol of formula HO-X is decarboxylated and saponified to generate cannabidivarin (VII).

13. The method according to claim 12, wherein the cannabidivarin, which is present after the decarboxylating saponification, is cyclised to trans-(−)-delta-9-tetrahydrocannabivarin (VIII).

14. The method according to claim 2, wherein the one, two, or more further extraction step(s) are carried out using an oil as the extracting agent.

15. The method of claim 4, wherein the conversion is carried out in a continuous process.

16. The method of claim 7, wherein the cannabidiol is cyclised in the absence of halogenated solvents.

17. The method according to claim 8, additionally comprising:
iii) subjecting the extract and/or the raffinate comprising the purified cannabinoid compound to one, two, or more further extraction step(s), wherein the extract and/or the raffinate respectively obtained in step iii) comprises the purified cannabinoid compound and less than 100 ppm in total of the olivetol.

18. The method according to claim 17, wherein the cannabinoid compound is trans-(−)-delta-9-tetrahydrocannabinol.

19. The method according to claim 17, wherein the cannabinoid compound is trans-(−)-delta-9-tetrahydrocannabivarin.

20. A method for purifying a cannabinoid compound obtained by enantiopure synthesis, wherein the cannabinoid compound is trans-(−)-delta-9-tetrahydrocannabinol or trans-(−)-delta-9-tetrahydrocannabivarin, the method comprising:
i) providing a mixture comprising the cannabinoid compound obtained by enantiopure synthesis, one or more of its isomers, and one or more further organic compounds, and ii) simultaneously,
- a) continuously feeding the mixture of step i) through a feed port into a simulated moving bed chromatographic apparatus comprising at least four columns connected in series and containing a stationary phase, and
- b) continuously feeding eluant into the apparatus through an eluant port, and
- c) continuously withdrawing the extract through an extract port, and
- d) continuously withdrawing the raffinate through a raffinate port, and iii) subjecting the extract and/or the raffinate comprising the purified cannabinoid compound to one, two, or more further extraction step(s),
- wherein the extract and/or the raffinate respectively comprises the purified cannabinoid compound, less than 100 ppm in total of any isomer(s) of the purified cannabinoid compound present in step i), and less than 100 ppm in total of olivetol.

\* \* \* \* \*